United States Patent [19]

Keller et al.

[11] Patent Number: 5,043,005
[45] Date of Patent: Aug. 27, 1991

[54] METHOD AND COMPOSITION FOR PRODUCING SPLIT-SHELL PISTACHIO NUTS

[76] Inventors: Charles H. Keller, 9005 Vista Rd.; Michael T. Hedberg, 13771 Ave. 18-1/2, both of Chowchilla, Calif. 93610

[21] Appl. No.: 158,567

[22] Filed: Feb. 22, 1988

[51] Int. Cl.$^5$ ..................... A01N 59/06; A01N 47/28
[52] U.S. Cl. .......................................... 71/65; 71/83; 71/119; 71/31
[58] Field of Search ..................... 71/65, 31, 33, 119, 71/83

[56] References Cited

U.S. PATENT DOCUMENTS

| 2,404,774 | 7/1943 | Dersch et al. | 430/399 |
|---|---|---|---|
| 3,594,362 | 7/1971 | Szabo | 71/119 |
| 3,846,116 | 11/1974 | Pearson | 71/65 |

OTHER PUBLICATIONS

Siegel N. and A. Haug Biochem. Biophys. Acta. 744: 36–45 (1983).
Berberich S. et al., Agricultural Res. 32(12): 8–11 (Sep. 1984).
Suhayda C. G. and A. Haug, Physiol. Plant. 68: 184–195 (1986).
Suhayda C. G. and A. Haug, Can. J. Biochem. Cell Biol. 63: 1167–1175 (1985).
Kinraide, T. B. and D. R. Parker, Physiol. Plant. 71: 207–212 (1987).

Primary Examiner—Richard L. Raymond
Assistant Examiner—B. Bembenick
Attorney, Agent, or Firm—Limbach, Limbach & Sutton

[57] ABSTRACT

Method and composition is disclosed for increasing the percentage of split-shell to non-split pistachio nuts produced during nut harvest by the pre-harvest application of an aluminum treatment to pistachio trees.

21 Claims, No Drawings

METHOD AND COMPOSITION FOR PRODUCING SPLIT-SHELL PISTACHIO NUTS

TECHNICAL FIELD

The present invention relates generally to the cultivation of pistachio nuts. More particularly, the invention relates to a new method for treating pistachio trees to increase the production of split-shell pistachio nuts, and to a composition for such treatment.

BACKGROUND OF THE INVENTION

The pistachio tree, *Pistacia vera*, is a deciduous tree noted for its edible nuts. Native to arid regions of Asia and Asia Minor, pistachio trees are grown primarily in the Mediterranean region, Italy, Turkey, Iran, Greece and The Soviet Union as a nut crop.

The green or reddish oval fruits, generally ¾ to 1 inch in length, are borne in clusters (racemes) on previous years vegetative growth of the pistachio tree. The fruit consists of an outer, fleshy hull (epicarp) containing a thin, tough shell. This hard shell contains the usually light-green nut kernel. The pistachio hull usually splits at maturity and is easily separated from the shell at harvest time.

The shell encasing the pistachio nut is divided by a longitudinal seam consisting of living cells. This seam splits, prior to nut harvest, in a fraction of the nut crop, resulting in a split-shell pistachio nut.

In harvesting pistachio nuts, the tree is shaken mechanically, to remove the nuts. The nuts are hulled immediately and dried.

The hulled nuts are separated from the blanks by an airleg or water bath flotation before drying and then sorted between split-shell pistachio nuts from intact-shell nuts ("non-splits"). The split-shell nuts are then generally roasted and salted, and typically sold as a popular snack food. As split-shells ease shelling by the consumer, these nuts command a higher price. The non-split nuts are cracked mechanically and the nut kernels are sold to the baking, ice cream and confectionery trade.

Although pistachio nuts are grown in California and other parts of the arid Southwest, a substantial commercial industry has been slow to develop in the United States, due in part to the long delay between initial tree planting and nut production.

Pistachio trees, producing both non-splits and split-shell nuts, are severely alternate bearing. In the "off years," non-splits account for 10 to 25% of the crop and the problem substantially worsens in the "on years." This imposes severe financial burdens on pistachio nut growers, since the market value of the non-splits is far below that of the split variety. For example, in 1986 approximately 55 million pounds of split-shell nuts and 20 million pounds of non-splits were produced from 40,000 acres, the non-splits representing over 38% of the average grower's crop (California Pistachio Commission Annual Report 1986/87). These nuts sold for $0.25 per pound before cracking, while the split-shell nuts commanded six times this amount, or $1.60 per pound. The growers' lost income amounted to approximately $25 million or over $600 per acre.

A resolution to the non-split problem has eluded both growers and university researchers. Experimenters have varied such parameters as fertilization, harvest timing, rootstock, nut variety and cultural practices, all to no avail. It would therefore be desireable to utilize a method to promote shell splitting in pistachio nuts prior to harvest. It would also be desireable to employ a composition which would promote shell splitting in pistachio nuts prior to harvest.

BACKGROUND ART

A general discussion on the pistachio nut crop can be found in *Tree Nuts*, AVI Publishing Co., Westport, Conn., pp. 572-603.

A discussion on the role of calcium and calmodulin in plant growth and development can be found in Poovaiah, B. W., Hort. Sci. 20(3):347-352 (1980) and in Berberich, S. et al. "Membrane Research—A Multidisciplinary Treasure Trove," in Agricultural Research, Beltsville Agricultural Research Center, 32(12):8-11 (September 1984).

Publications which disclose the use of organic acids as chelating agents to reduce aluminum toxicity in cells include Suhayda, C. G. and A. Haug, Can. J. Bio. Chem. Cell Biol. 63:1167-1175 (1985) and Physiol. Plant. 68:189-195 (1986).

DISCLOSURE OF THE INVENTION

It has been unexpectedly found that the percentage of split-shell pistachio nuts produced per tree can be increased by exposing trees to an aluminum treatment prior to nut harvest. This surprising new method will enable growers to produce increased quantities of split-shelled nuts, thus alleviating the serious financial impact imposed by the large numbers of intact-shell nuts currently harvested. Additionally, the novel composition may have other useful applications in the agricultural industry.

In accordance with one aspect of the present invention, an aluminum treatment is applied to pistachio trees for times and under conditions sufficient to increase the proportion of split-shell nuts to non-split nuts, relative to trees not so treated. The aluminum treatment can be applied, e.g., foliarly or systemically to produce the desired results.

Also provided is a novel composition to be utilized in accordance with aspects of the present invention, as well as for other agricultural purposes. This composition comprises a mixture of an aluminum in a form capable of producing free ion, and a wetting agent, in an appropriate solvent. Optionally, a cuticle softening agent will also be included in the composition.

DETAILED DESCRIPTION OF THE INVENTION

In accordance with the present invention, a novel method for treating pistachio trees is provided which significantly increases the percentage of split-shell pistachio nuts produced on treated trees. The present disclosure also provides a new composition to be used in practicing certain aspects of the present invention.

Although not intending to be bound by any particular theory, a probable foundation for the present invention is that a non-split nut is the normal, viable seed of a mature, healthy tree. A split-shell nut is an aborted seed, which is discarded by the tree.

It is known that pistachio trees, producing both non-splits and split-shell nuts, are severely alternate bearing. In an "on" year the tree has substantial energy reserves and devotes a great deal of energy to vegetative growth and production of seeds. Therefore, non-split nuts account for a greater proportion of the crop because the tree had substantial energy reserves.

After this great expenditure of energy, the tree experiences an "off" year and its low energy reserves result in an increase in the number of split-shelled nuts. Thus, the normal horticultural practices designed to increase the health and longevity of pistachio trees actually contribute to the increase in non-split nuts and the decreased profitability of the nut crop.

Thus, it was determined that some means of selectively weakening the seam of the pistachio nut shell, without substantially harming the tree, would increase the split-shell nut productivity.

Although the practice of this invention does not depend on the accuracy of the particular theory, it is probable that the benefits of the invention result from some disruption in the cells making up the seam of the shell. Support for this theory is provided by the recent finding that calcium modulating protein, known as calmodulin, may bind aluminum (Siegel, N. and A. Haug, Biochem. Biophys. Acta. 744:36-45 (1983)). Calmodulin is an intracellular protein which, upon activation by calcium, binds to protein receptors which function to maintain cell wall integrity. It is also known that calmodulin plays an important role in plant growth and development (Poovaiah, B. W., Hort. Sci. 20(3):347-352 (1980)).

Aluminum, on the other hand, is not considered a micronutrient for most crops, but rather displays toxic effects in plants (Berberich, S. et al., Agricultural Res. 32(12):8-11 (September 1984)). Aluminum is principally used in agriculture as a component of fertilizer compounds to change the foliage color of plants. Particular effects of aluminum on pistachio trees or nuts are not known to have been previously reported.

Recent investigators have hypothesized that aluminum interferes with calcium metabolism by binding to and causing a resultant change in calmodulin structure and function (Siegel, et al., supra). This alteration renders calmodulin ineffective, thereby causing changes in cell wall rigidity and demonstrating cytotoxic effects (Berberich, S. et al., supra).

As the seam along the longitudinal axis of the pistachio nut shell consists of living cells, this change in calmodulin structure may cause or accelerate mortality in these cells, and may be responsible for the increased splitting in pistachio nut shells observed during the practice of the present invention. However, it may be that aluminum has a different interaction with calmodulin which causes the increase in shell-splitting, or its site of action may be entirely separate from calmodulin.

Therefore, without regard to the actual causal mechanism, one aspect of the invention provides a method wherein an aluminum treatment is applied to pistachio trees for times and under conditions sufficient to increase the proportion of split-shell nuts to non-split nuts, relative to trees not so treated.

In accordance with another aspect of the present invention, a composition comprising aluminum in a form capable of producing free ion, a wetting agent and, optionally, a cuticle softening agent, is applied to the foliage of pistachio trees prior to harvest.

The aluminum treatment is most usually carried out not more than 60 days before the crop is ready for harvest, desirably between 30 and 90 days prior to harvest, said treatment being effected so as to maintain a sufficient level of aluminum in the pistachio nuts so as to increase the amount of shell-splitting thereby. The timing, duration and conditions of the treatment may be adjusted to accommodate various modes of application, environmental conditions and other factors.

In practicing the invention, an aluminum treatment may be used at rates of from 0.1 to 20 kg of aluminum in a form capable of producing free ion, per acre, so as to provide a dosage of approximately 0.001 to 0.1 kg per tree. It will be understood that the amount of aluminum treatment employed per acre or per tree will depend in part on the mode of application, the concentration of aluminum available to affect the tree, number of trees per acre and numerous other factors.

The treatment of the present invention can be applied by any means which will increase the concentration of ionic aluminum in the nuts and probably in the cells of the longitudinal seam. However, although a common method of treating plants consists of applying the desired substance to the soil, with subsequent uptake through the root system, this method may be less desirable for the treatment of the present invention. The pistachio tree is known is have a low rate of uptake through its root system. In addition, it is known that aluminum is toxic to plant root tissue and, being highly polar, it would be slow to translocate from the root system, thereby further delaying its desired benefits and increasing its toxic effects on root cells.

Desirable methods of applying the present aluminum treatment include foliar application or direct systemic application. Direct systemic application of the aluminum treatment to a pistachio tree can be performed, for example, by injection or by introducing metallic aluminum directly into the trunk or limbs, e.g., with nails, spikes, glaziers points, or other members containing aluminum. However, the metallic aluminum method of direct systemic application may not allow precise monitoring of aluminum translocation and the resultant toxic effects.

Direct injection can be performed by means well known in the art of horticulture, for example by following protocols used to inject systemic fungicides for the control of vascular wilts. The aluminum treatment to be injected may be mixed in any suitable solvent and injected as desired. Due to the low rate of translocation of aluminum through the pistachio tree, systemic injection should minimize aluminum toxicity effects on root cells.

Such a mixture can include simply an aqueous solution of any source of aluminum ions wherein the aluminum as free ion is in a proportion of from approximately 0.01 to 10.0 percent, more usually 0.05 to 5.0 percent and desirably 0.05 to 2.5 percent by weight of the total solution, pH adjusted to a value less than 7.0, desirably less than 5.0.

However, it is considered more desirable to apply the treatment of the present invention by foliar application. Foliar application of the present aluminum treatment affords several advantages over root uptake. First, the pistachio tree has a low rate of uptake through the root system and foliar application allows a more direct route to the nut cluster. Additionally, higher levels of aluminum will likely be found tolerable by the tree, since aluminum is highly polar and will tend not to translocate out of the leaves and rachis to the root, where accumulation and subsequent tree damage might occur.

Desirably, substances which may be used in the aluminum treatment of the present invention will not affect the palatability or subsequent edibility of nuts which are destined to be harvested. The aluminum treatment of the invention will contain at least one form of aluminum which is capable of exhibiting cytotoxic effects. Typically, this will include free $Al^+$ ions or any aluminum-containing compound that ionizes in solution to produce $Al^+$ ions including, e.g., $Al_2(SO_4)_3$. Of particular value, the aluminum-containing compound employed in the present method is preferably aluminum sulphate or alum (a soluble aluminum sulphate and potassium salt). Such aluminum-containing compounds are often found in fertilizers containing an aluminum component. A particularly desirable form of aluminum sulphate is 96% $AlSO_4$ (food grade, available from Allied Chemical Co.) as used in pickling cucumbers and other foods.

The following compounds are presently considered to be suitable for the practice of the present invention, without attempting to provide an exhaustive list thereof:

Table I

Aluminum sulphate
Alum (Aluminum potassium sulphate)
Aluminum ammonium sulphate
Aluminum sodium sulphate
Aluminum chloride
Aluminum hydroxide
Aluminum nitrate In addition, aluminum and aluminum-containing compounds are often contained in other agricultural chemicals, including fungicides. For example, Aliette ®, Mikal ®, and Phodax ® (proprietary compounds composed of aluminum tris-O-phosphonate from Rhone-Poulenc, France) can be employed as aluminum-containing compounds in the practice of the present invention. Thus it will be recognized that many forms of aluminum can be employed in the practice of the invention, so long as they demonstrate the requisite increase in pistachio nut shell splitting.

It is also considered useful to include, in certain treatments particularly adapted for foliar application, a surfactant or wetting agent. The wetting agent functions to alter the surface properties of the pistachio tree leaves, in order to facilitate absorption of the aluminum treatment of the invention. In the practice of the invention, a wetting agent will also desirably not exhibit adverse effects on the foliage, nor interfere with the remaining active components of the aluminum treatment.

Suitable wetting agents include, but are not limited to, non-ionic detergents such as Triton X ® (proprietary compounds from Rohm & Haas composed of octoxynol); polysorbate compounds such as one of the Tween ® compositions (ICI Americas), or Nonidet ® (ethylene oxide condensates from Shell Chemical Co.), among others.

It has also been found desirable, in certain applications, to employ commercially available detergents, such as Palmolive ® liquid detergent (a proprietary product of the Colgate-Palmolive Co.) as wetting agents in compositions for foliar application. It will be understood that numerous additional wetting agents may be employed, either separately or in combination, in the practice of the present invention.

A selected wetting agent can be included, if desired, at a concentration of from approximately 0.001 to 1.0 percent of the solution, more usually from approximately 0.005 to 0.5 percent. Alternatively, it would be possible to pre-treat the foliage of the pistachio tree with a wetting agent, or to so treat the foliage after the present aluminum treatment, and retain the benefits of this component of the present invention.

An additional desirable component of an aluminum treatment composition for foliar application can include a cuticle softening agent, such as urea, to soften the waxy, water-resistant coating of the leaf. Such an agent would further facilitate absorption of the aluminum treatment into the leaf, so that transport through the conductive tissues into the nut can occur more readily.

In formulating an aluminum treatment of the invention for systemic or foliar application, the various components will ordinarily be dissolved in at least one solvent which does not substantially adversely affect the aluminum, the wetting agent, the pistachio tree or the nuts produced therefrom. Many such solvents exist, and water is considered desirable due to its ready availability and low cost.

It may also be desireable to adjust the pH of the aluminum treatment, as the aluminum is more mobile at acidic pH values.

The amount of aluminum treatment required to obtain the desired effect will be found to vary according to conditions affecting uptake. Desirable results can be achieved with an aluminum treatment composed of 96% aluminum sulphate at 10 to 50 pounds per 150 gallons of water per acre of trees, assuming between 135 and 150 pistachio trees per acre. It is to be understood that these figures represent reasonable approximations. However, the upper and lower limits of these parameters will vary depending on many factors including soil pH, the mode of application, the skill and care exercised by the operator, avoidance of waste, and climatic factors such as temperature, the amount of rainfall subsequent to foliar application, among others.

After an aluminum treatment is applied by any of the foregoing methods and nut harvest has terminated, it may be desirable to reduce the amount of residual aluminum in the tree, in order to avoid growth retardation or flower-bud mortality which might affect subsequent harvests. As one means of alleviating such damage, an aluminum chelating compound may be applied to the treated tree in order to bind and remove excess free aluminum ion. Exemplary of such chelating compounds are organic acids, which provide effective ligands for aluminum complexation (Suhayda, C. G. and A. Haug, Physiol. Plant. 68:189-195 (1986); Suhayda, C. G. and A. Haug, Can. J. Biochem. Cell Biol. 63:1167-1175 (1985)). These acids are generally dicarboxylic acids wherein the carboxyl groups are separated by a chain of five or less carbon atoms, e.g.

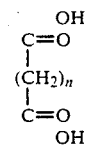

Alternatively, the carbon chain in an organic acid can include CHOH groups replacing one or more $CH_2$ groups. Representative organic acids include oxalic, malonic, citric, succinic, glutaric, maleic, pimelic and tartaric acids, among others. In particular, a citrate addition (e.g., as $K_2$-citrate) is considered a desirable chelating agent for the complexation and removal of excess free aluminum ion.

Alternatively, a calcium ion source can be applied to the trees, preferably, but not necessarily, by foliar application. The calcium source can be calcium nitrate or any other calcium compound capable of restoring the aluminum-calcium balance, and reversing the cytotoxic aluminum effects.

However, it appears that aluminum sulphate ions may be non-phytotoxic (Kinraide, T. B. and D. R. Parker, Physiol. Plant. 71:207-212 (1987)). Therefore, of all sources of aluminum ion capable of being used in the aluminum treatment of the invention, aluminum sulphate appears to be the most desirable.

The practice of the present invention is illustrated by the following examples without, however, implying any limitation to the scope of this invention.

Experimental

In the examples which follow, all percentages are expressed by weight, unless otherwise indicated.

EXAMPLE 1

This example describes foliar application of the aluminum treatment of the present invention.

Samples of aluminum treatment prepared in accordance with the invention contained the following formulations:

TABLE II

| Ingredients | Sample No. 1 | Sample No. 2 |
|---|---|---|
| | (weight in kilograms) | |
| Aluminum sulfate (95%) | 7.25 | 14.0 |
| Palmolive ® detergent | 0.5 | 0.5 |
| Water | 572 | 572 |

The samples were prepared by stirring 16 and 31 pounds of 96% aluminum sulphate, respectively, and 16 ounces of Palmolive ® detergent in 150 gallons of water containing at room temperature until all solids were completely dissolved. The pH of the final solution was less than 3.0. The addition of aluminum sulfate according to each formulation above produced an aluminum treatment with approximately 1,500 ppm $Al^+$ in sample No. 1 and 3,000 ppm $Al^+$ in sample No. 2. A control sample containing Palmolive ® detergent and water was also employed.

Each sample was applied directly to the foliage of an individual tree by spraying from a hand sprayer. The application continued until the foliage was saturated, generally until fluid run-off from the leaf was observed.

In order to increase the concentration of aluminum in the nut, without excess toxic reaction, different concentrations were applied for different times, thereby maintaining high $Al+$ concentrations for a sufficient period of time before nut harvest. The results, presented as the percentage of split-shell nuts for each treatment were as presented in Table III.

TABLE III

| Sample | % Split-Shells |
|---|---|
| 1 | 96% |
| 2 | 98% |
| Control | 92% |

EXAMPLE 2

In a second trial of foliar application of the aluminum treatment of the present invention, samples of aluminum treatment prepared in accordance with the formulations of Example 1, but containing 31 pounds (Sample 3) and 44 pounds (Sample 4) of 96% aluminum sulphate. The addition of aluminum sulfate according to each formulation above produced an aluminum treatment with approximately 3,000 ppm $Al^+$ in sample No. 3 and 4,500 ppm $Al^+$ in sample No. 4. A control sample containing Palmolive ® and water was also employed.

Each sample was applied directly to the foliage of an individual tree by spraying from a low-volume electrostatic sprayer (Windmill ®, Modesto, Calif.). The application continued until the foliage was saturated, generally until fluid run-off from the leaf was observed.

The results, expressed as the percentage of split-shell nuts for each treatment, are shown in Table IV.

TABLE IV

| Sample | % Split-Shells |
|---|---|
| 3 | 99.75% |
| 4 | 99.5% |
| Control | 98% |

It was found that approximately thirty days were required after application of the treatment solution for the $Al^+$ concentration to reach the desired level in the nut. Earlier treatment at lower $Al^+$ concentration and later treatment at higher $Al^+$ concentrations will also produce the desired shell splitting effects.

Excessive application of the present aluminum treatment can cause foliar deterioration and possible loss of next season's flower buds. Thus, it is considered preferable to apply the solutions as close to harvest as possible, keeping in mind that higher than normal $Al^+$ concentrations are required in the nut to promote splitting.

It should be noted that both Examples above were performed during an "off" year for pistachio nut harvest, when the relative proportion of split-shelled nuts in a normal crop is high. Assuming that all other factors are equal, the improvement obtained through the practice of the present invention during an "on" year will be even more dramatic, as the split-shell percentage in the control samples will be substantially reduced.

EXAMPLE 3

This example illustrates a systemic application method in accordance with the present invention.

An aluminum treatment was prepared by mixing approximately 9 g of Aliette ® (Rhone-Poulenc, France) with IL, wherein the aluminum is present as aluminum tris-o-ethyl phosphonate. The pH of the solution was adjusted to approximately 2.0 with hydrochloric acid.

This solution was injected into the trunk of a pistachio tree during June by using a high-pressure tree injector which uses a 2½ horsepower engine to develop 600-700 psi and force the treatment solution into the tree through a drilled-out lag bolt brazed to a high pressure coupling.

Approximately 10 days after the aluminum treatment, it was observed that all nuts on the primary limb above the injection site were split. It is known that pistachio nut shell splitting does not normally occur in July. Thus the shell splitting response was due to the external stimulus induced by the aluminum treatment.

In every Example above, samples from aluminum treatment field trials always displayed higher $Al+$ concentrations in split-shelled nuts and higher percentage of split-shell nuts than control trees not subject to the aluminum treatment.

It was determined in one experiment that the total aluminum level in split-shell pistachio nuts was 225% of the aluminum level in non-split nuts. It was also noted that there was a 1300% difference in aluminum levels in the hulls, a 135% difference in the shells and no difference in aluminum levels in the meats. This clearly indicates that the site of action of the aluminum is most likely in the hull and shell of the pistachio nut.

Aluminum sulphate has been determined to be non-phytotoxic (Kinraide, T. B. and D. R. Parker, Physiol. Plant. 71: 207-212 (1987)) and is generally recognized as safe and approved by the Food and Drug Administration as a miscellaneous and/or general purpose food additive (21 C.F.R. 182.1125). It is available as iron-free, food grade liquid alum or as a low-iron granular product (non-food grade) from General Chemical (Middletown, Ohio).

In addition, it is expected that split-shell nuts treated in accordance with the present invention would not present any problem with increased aluminum levels in the portion consumed, as the above results demonstrate.

Therefore, it can be seen that the practice of this invention provides an increase in the proportion of split-shelled pistachio nuts in a crop without substantial risk of damage to the tree or the food crop.

Although the foregoing invention has been described in some detail, it will be understood that various modifications of the invention may be practiced while remaining with the scope of the appended claims.

We claim:

1. A method for treating pistachio trees to increase the percentage of split-shell pistachio nuts produced which comprises:
   exposing pistachio trees prior to nut harvest, to aluminum in a form capable of producing free ion for times and under conditions sufficient to increase the proportion of split-shell nuts to non-split nuts, relative to trees not so treated.

2. A method as recited in claim 1 wherein the aluminum in a form capable of producing free ion comprises at least one aluminum salt.

3. A method as recited in claim 2 wherein said aluminum treatment comprises a fertilizer or a fungicide suitable for application to said trees.

4. A method as recited in claim 2 wherein said trees are exposed to the aluminum treatment by foliar application.

5. A method as recited in claim 4 wherein the aluminum treatment is a mixture further comprising a wetting agent.

6. A method as recited in claim 5 wherein the wetting agent comprises a non-ionic detergent.

7. A method as recited in claim 5 wherein said wetting agent is selected from the group consisting of Triton X ®, Tween ®, Nonidet ® and Palmolive ® liquid detergent.

8. A method as recited in claim 5 wherein the mixture further comprises a cuticle softening agent.

9. A method as recited in claim 8 wherein said cuticle softening agent comprises urea.

10. A method as recited in claim 1 wherein said trees are exposed to the aluminum treatment by systemic application.

11. A method for treating pistachio trees as recited in claim 10 wherein said systemic application comprises introducing at least one aluminum containing member directly into the tree trunk or branches of said trees.

12. A method for treating pistachio trees as recited in claim 10 wherein said systemic application comprises introducing the aluminum treatment into the trunk or branches of said trees by injection.

13. A method as recited in claim 1 wherein the method further comprises applying at least one aluminum chelating compound to said treated trees subsequent to nut harvest.

14. A method as recited in claim 13 wherein said aluminum chelating compound comprises an organic acid.

15. A method as recited in claim 14 wherein said organic acid is at least one member selected from the group consisting of oxalic acid, malonic acid, citric acid, succinic acid, glutaric acid, maleic acid, pimelic acid, and tartaric acid.

16. A composition for treating pistachio trees to increase the percentage of split-shell pistachio nuts produced which comprises:
   Aluminum as free ion in a proportion of from approximately 0.001 to 10.0 percent by weight of the total composition;
   At least one wetting agent in a proportion of from approximately 0.0001 to 1.0 percent by weight of the total composition; and
   At least one solvent which does not substantially adversely affect the aluminum, the wetting agent, the pistachio tree or the nuts produced therefrom.

17. A composition as recited in claim 16 wherein the wetting agent is at least one member selected from the group consisting of Triton X ®, Tween ®, Nonidet ® and Palmolive ® liquid detergent.

18. A composition as recited in claim 16 wherein the Aluminum ion is in a proportion of from approximately 0.01 to 5.0 percent by weight of the total composition.

19. A composition as recited in claim 16 wherein the wetting agent is in a proportion of from approximately 0.001 to 0.1 percent by weight of the total composition.

20. A composition as recited in claim 16 further comprising at least one cuticle softening agent in a proportion of from approximately 0.001 to 1.0 percent by weight of the total composition.

21. A composition as recited in claim 20 wherein the cuticle softening agent comprises urea.

* * * * *